United States Patent [19]
Aoki et al.

[11] 4,297,440
[45] Oct. 27, 1981

[54] COLOR PHOTOGRAPHIC LIGHT-SENSITIVE ELEMENT

[75] Inventors: Kozo Aoki; Satoru Sawada; Yoshiharu Yabuki; Nobuo Furutachi, all of Minami-ashigara, Japan

[73] Assignee: Fuji Photo Film Co., Ltd., Minami-ashigara, Japan

[21] Appl. No.: 210,184

[22] Filed: Nov. 25, 1980

[30] Foreign Application Priority Data

Nov. 26, 1979 [JP] Japan ................................. 54-153359

[51] Int. Cl.³ .......................... G03C 1/76; G03C 1/40
[52] U.S. Cl. ..................................... 430/505; 430/554; 430/555; 430/558; 430/551
[58] Field of Search ................ 430/554, 555, 558, 505

[56] References Cited
U.S. PATENT DOCUMENTS

| | | | |
|---|---|---|---|
| 2,311,082 | 2/1943 | Porter et al. | 430/554 |
| 3,684,514 | 8/1972 | Iwama et al. | 430/555 |
| 3,928,044 | 12/1975 | Arai et al. | 430/555 |
| 3,935,015 | 1/1976 | Arai et al. | 430/554 |
| 4,220,470 | 9/1980 | Furutachi et al. | 430/558 |

Primary Examiner—J. Travis Brown
Attorney, Agent, or Firm—Sughrue, Mion, Zinn, Macpeak and Seas

[57] ABSTRACT

A color photographic light-sensitive element is described comprising a support having thereon a silver halide emulsion layer containing therein a 3-anilino-5-pyrazolone magenta color-forming coupler represented by formula (I)

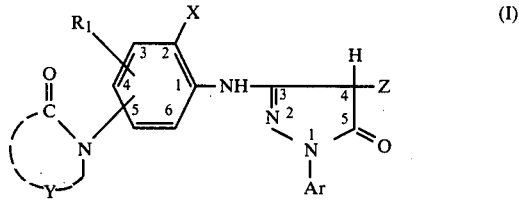

wherein X represents a halogen atom or an alkoxy group; Ar represents an aryl group; $R_1$ represents hydrogen, a halogen atom, an alkyl group, an alkoxy group or an alkylthio group; Y represents a non-metallic atomic group forming a 5-membered or 6-membered ring together with the

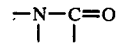

group, except that Y does not include a carbonyl group; and Z represents hydrogen or a coupling-off group.

The magenta color images obtained after color development processing of the color photographic light-sensitive element have an excellent light-fastness, and the formation of yellow stain in the unexposed areas thereof is prevented.

12 Claims, No Drawings

COLOR PHOTOGRAPHIC LIGHT-SENSITIVE ELEMENT

BACKGROUND OF THE INVENTION

The present invention relates to silver halide photographic light-sensitive elements containing a novel magenta color forming coupler.

After image-wise exposing a silver halide photographic light-sensitive element to light, the element is developed using an aromatic primary amine developing agent. The developing agent is oxidized by color development and reacts with a coupler to form a dye, and thus a color image is formed. In this system, a subtractive method is generally used for color reproduction, in which blue, green, and red colors are reproduced by forming yellow, magenta, and cyan color images which are in complementary relationship thereto, respectively. In general, acylacetamide or dibenzoylmethane type couplers are employed for forming yellow color images; pyrazolone, cyanoacetyl, or indazolone type couplers are used for forming magenta color images, and phenol-type couplers, for example, phenols and naphthols, are utilized for forming cyan color images.

To produce color photographs, couplers which form dyes are incorporated into a developer or are present in a light-sensitive photographic emulsion layers.

A variety of 5-pyrazolone type couplers for forming magenta color images are known. Known substituents at the 3-position of the 5-pyrazolone ring include an alkyl group, an aryl group, alkoxy groups as described in U.S. Pat. No. 2,439,098, acylamino groups as described in U.S. Pat. Nos. 2,369,489 and 2,600,788, ureido groups as described in U.S. Pat. No. 3,558,319, and an anilino group. 3-Anilino-5-pyrazolone type couplers have often been described in the art since U.S. Pat. No. 2,311,081 (U.S. Pat. No. Re. 22,329) was issued, and several improvements therein have been proposed. British Pat. No. 956,261 discloses that azomethine dyes obtained from derivatives in which the ortho position of the anilino group is substituted with an alkoxy group or a halogen atom have advantageous spectral absorption properties for color photography, in that undesired absorption in the red light region is particularly low.

Specific examples of diffusion resistant couplers which belong to this type and are capable of being incorporated into photographic emulsions are described in U.S. Pat. Nos. 3,684,514, 3,930,861, 3,907,571, 3,928,044, 3,926,634 and 3,935,015, Japanese Patent Application (OPI) No. 123033/74 (the term "OPI" as used herein refers to a "published unexamined Japanese patent application"), and so forth. For example, the couplers described in U.S. Pat. No. 3,935,015 are well known, being 3-(acylaminoanilino)-5-pyrazolones represented by the formula (M)

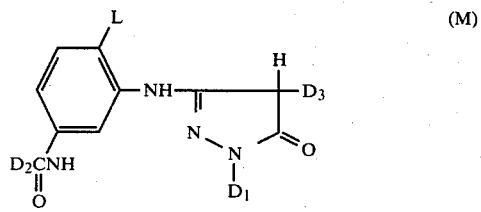

(M)

wherein $D_1$ represents an aryl group or a heterocyclic group, $D_2$ represents a straight chain, branched chain, or cyclic alkyl group having from 7 to 23 carbon atoms, $D_3$ represents a coupling-off group, and L represents an alkoxy group having from 1 to 18 carbon atoms or a halogen atom.

These couplers have the characteristics that the undesired absorption of magenta azomethine dyes obtained upon color formation using the same in the red light region is low, the cut-off of the main absorption is good at the longer wavelength side, and magneta color images having a high color density are obtained because the coupling speed is high. Furthermore, the solubility in organic solvents having a high boiling point is improved so that, after dissolving these couplers in organic solvents, the couplers can be emulsion-dispersed in an aqueous medium in the form of fine colloidal particles and then added to emulsions.

However, these couplers have the disadvantages that the degree of yellow staining at the unexposed portion after color development processing is high, and this degree of yellow staining is increased upon irradiation with light. Furthermore, they have the disadvantages that color fading of the magenta color images obtained upon color development using these compounds occurs to a significant degree upon irradiation of the formed image with light, and the color balance required for color photography is damaged by subsequent exposure to light, since, for example, in a color film or a color paper, particularly in a color paper, the color images are formed when three colors such as yellow, magenta and cyan combine with each other, but among these colors, the magenta color is not faster than any other color upon light irradiation. These disadvantages become fatal defects for color light-sensitive elements, such as color printing papers and the like. Thus, improved couplers which do not have these disadvantages have been strongly desired.

SUMMARY OF THE INVENTION

A first object of the present invention is to provide a coupler with which the formation of yellow stain in the unexposed areas of a coupler photographic light-sensitive element after color development processing is minimized, and, further with which yellow stain does not occur upon irradiation of the formed image with light.

A second object of the present invention is to provide a coupler having the property that color images formed therefrom are stable with respect to fading, even if the magenta color images obtained after color development are irradiated with light.

A third object of the present invention is to provide a light-sensitive element which is suitable for a simple development processing without stabilizing processing with formaldehyde or the like being required.

A fourth object of the present invention is to provide a novel coupler which has a high color formation rate and provides magenta color images having a high density.

A fifth object of the present invention is to provide a coupler which has excellent solubility in an organic solvent and is suitable for use in a method which comprises emulsion-dispersing the coupler in an aqueous medium in the form of fine colloidal particles and then incorporating the dispersion into an emulsion.

These and other objects of the present invention will become more apparent from the detailed description of the invention and the examples provided hereinbelow.

These objects are effectively achieved by a color photographic light-sensitive element containing in a silver halide photographic emulsion layer thereof, as a magenta color image-forming coupler, a 3-anilino-5-pyrazolone coupler wherein the anilino group thereof is substituted with a halogen atom or an alkoxy group at the 2-position of the anilino group and with a lactam group at the 4- or 5-position of the anilino group, and an aryl group is present at the 1-position of the pyrazolone nucleus. Further, the 4-position of the pyrazolone nucleus is substituted with at least one hydrogen, or may be substituted with another hydrogen or a coupling-off group.

DETAILED DESCRIPTION OF THE INVENTION

The term "coupling-off group" as used herein has the same meaning as when generally used in the color-forming coupler field and refers to a group other than hydrogen which is eliminated by the oxidation product of an aromatic primary amine developing agent during the coupling reaction.

Couplers which are useful for the present invention include compounds represented by the formula (I)

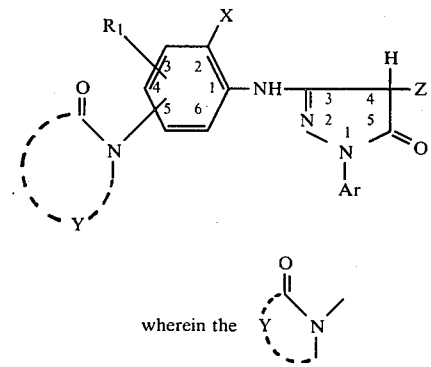

wherein the 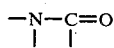

group is present at the 4- or 5-position of the anilino group; X represents a halogen atom or an alkoxy group; Ar represents an aryl group; $R_1$ represents hydrogen, a halogen atom, an alkyl group, an alkoxy group, or an alkylthio group; Y represents a non-metallic atomic group forming a 5-membered or 6-membered ring together with the $$-N-C=O$$

group, except that Y does not include a carbonyl group; and Z represents hydrogen or a coupling-off group.

X, Z, Ar, $R_1$ and Y in the formula (I) above are described in detail below.

In formula (I), X preferably represents a halogen atom (for example, a chlorine atom, a bromine atom, etc.) or an alkoxy group having from 1 to 22 carbon atoms (for example, a methoxy group, an ethoxy group, a heptoxy group, a tetradecyloxy group, a hexadecyloxy group, an octadecyloxy group, a dodecyloxy group, an allyloxy group, a benzyloxy group, a phenethyloxy group, etc.). The alkoxy group can be substituted with one or more substituents selected from a halogen atom, a nitro group, a cyano group, an alkoxy group (for example, a methoxy group, an ethoxy group, etc.), an aryloxy group (for example, a phenyloxy group, a naphthyloxy group, etc.), an alkylcarbonyl group (for example, an acetyl group, a tetradecanoyl group, etc.), an alkoxycarbonyl group (for example, a methoxycarbonyl group, a benzyloxycarbonyl group, etc.), an acylamino group (for example, an acetylamino group, a benzamido group, etc.), a sulfonamido group (for example, a methanesulfonamido group, a p-toluenesulfonamido group, etc.), a hydroxy group and a mercapto group. Where X is an alkoxy group substituted with a fluorine atom, X can also be a so-called polyfluoroalkoxy group.

In formula (I), Z can represent hydrogen, or a coupling-off group. Suitable coupling-off groups represented by Z include, for instance, a thiocyano group, an acyloxy group (for example, an acetoxy group, a dodecanoyloxy group, an octadecanoyloxy group, a 3-pentadecylphenoxyacetoxy group, a benzoyloxy group, a β-naphthoyloxy group, a 3-[γ-(2,4-di-tert-anylphenoxy)butyramido]benzoyloxy group, etc.), an aryloxy group (for example, a phenoxy group, a p-chlorophenoxy group, a p-nitrophenoxy group, a naphthoxy group, etc.), an alkoxy group, a halogen atom (for example, a chlorine atom, a fluorine atom, etc.), an arylazo group (for example, a phenylazo group, a 2-methyl-4-hydroxyphenylazo group, a naphthylazo group, etc.), an aryltriazolyl group (for example, a 1-benzotriazolyl group, a 2-benzotriazolyl group, a 2-naphthotriazolyl group, etc.), an alkylthio group (for example, an alkylthio group having 2 to 22 carbon atoms, etc.), an arylthio group (for example, a phenylthio group, a naphthylthio group, etc.), an aralkoxycarbonyloxy group (for example, a benzyloxycarbonyloxy group, etc.), an alkoxycarbonyloxy group, an aryloxycarbonyloxy group, a heterocyclic thio group (for example, a 2-benzothiazolylthio group, a 1-phenyl-5-tetrazolylthio group, a 2-benzoxazolylthio group, a 2-benzimidazolylthio group, a 5-phenyl-1,3,4-oxadiazolyl-2-thio group, etc.), a cycloalkylthio group (for example, a cyclohexylthio group, etc.), a cycloalkoxy group (for example, a cyclohexyloxy group, etc.), an imido group (for example, a phthalimido group, a succinimido group, a 5,5-dimethyl-3-hydantoinyl group, a 5,5-dimethyl-3-oxazolidinyl group, etc.), an imidazolyl group (for example, a 1-imidazolyl group, a 2-methyl-1-imidazolyl group, a 1-benzimidazolyl group, etc.), a pyrazolyl group (for example, 1-pyrazolyl group, a 4-chloro-1-pyrazolyl group, etc.), a triazolyl group (for example, a 3,5-diethyl-1,2,4-1-triazolyl group, etc.), an acylamino group (for example, a benzamido group, an acetylamino group, etc.), a sulfonamido group (for example, a benzenesulfonamido group, a methanesulfonamido group, etc.), a cycloamino group (for example, a piperidino group, a morpholino group, etc.), or the like.

In formula (I), Ar represents an aryl group (for example, a phenyl group or a phenyl group substituted with one or more substituents such as a halogen atom, a cyano group, an alkyl group, an alkoxy group, an acylamino group, a sulfamoyl group, a sulfamido group, a carbamoyl group, an alkoxycarbonyl group, an alkylsulfonyl group, an alkylthio group, a nitro group, or a trifluoromethyl group, and more preferably a 2-chlorophenyl group, a 4-chlorophenyl group, a 2,5-dichlorophenyl group, a 2,6-dichlorophenyl group, a 2,4,6-trichlorophenyl group, a 2-bromophenyl group, a 3,5-dibromophenyl group, a 2-cyanophenyl group, a 2,6-dichloro-4-cyanophenyl group, a 4-cyanophenyl group, a 4-methylphenyl group, a 2,6-dimethylphenyl group, a 4-butylphenyl group, a 2-trifluoromethylphenyl group, a 2-ethoxyphenyl group, an N-methylbenzamidophenyl group, an N,N-diphenylsulfamoylphenyl group, a phenyl-N-methylsulfonamidophenyl group, a 2,6-dichloro-4-[α-(2,4-di-tert-amylphenoxy)-butanamido]phenyl group, a 2,6-dichloro-4-tetradecyloxycarbonylphenyl group, a 2,6-dichloro-4-octadecyloxyphenyl group, a 2,6-dichloro-4-hexadecylthiophenyl group, a 2,6-dichloro-4-octadecylsulfonylphenyl group, a 4-tetradecylcarbamoylphenyl group, a 2,3,4,5,6-pentafluorophenyl group, a 2,3,4,5,6-pentachlorophenyl group, a 2-chloro-5-cyanophenyl group, a 5-chloro-2-methylphenyl group, a 2,6-dichloro-4-methylphenyl group, a 2,4-dichloro-6-methylphenyl group, a 2-chloro-4,6-dimethylphenyl group, a 2,6-dichloro-4-methoxyphenyl group, etc.).

In formula (I), $R_1$ represents hydrogen, a halogen atom (for example, a chlorine atom, a bromine atom, etc.), an alkyl group (for example, a methyl group, an ethyl group, a propyl group, a tert-butyl group, an n-octyl group, an n-dodecyl group, an n-hexadecyl group, etc.), an alkoxy group (for example, a methoxy group, an ethoxy group, a propoxy group, a 2-ethylhexyloxy group, a benzyloxy group, a dodecyloxy group, a hexadecyloxy group, etc.), or an alkylthio group (for example, a methylthio group, an ethylthio group, a hexylthio group, a dodecylthio group, a tetradecylthio group, etc.).

In formula (I), Y represents a non-metallic atomic group forming a 5-membered or 6-membered ring together with the

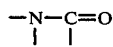

group. In more detail, the nucleus represented by the formula of

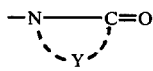

preferably is selected from the group consisting of:

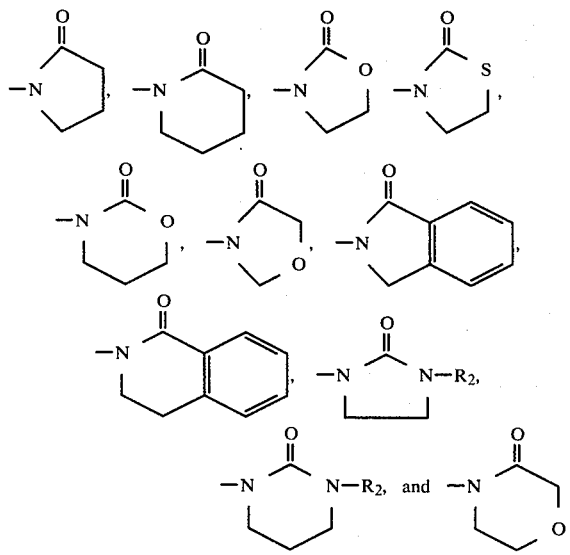

These nuclei may be substituted with one or more substituents. Examples of the substituents include a straight chain or branched chain alkyl group having from 1 to 22 carbon atoms, an alkenyl group, a cycloalkyl group, a cycloalkenyl group, an aralkyl group having from 2 to 32 carbon atoms, a carboxy group, an alkoxy group having from 1 to 22 carbon atoms, a halogen atom, a cyano group, an aryl group having from 6 to 32 carbon atoms, an alkylcarbonyl group having from 2 to 22 carbon atoms, an arylcarbonyl group having from 7 to 32 carbon atoms, an alkoxycarbonyl group having from 2 to 22 carbon atoms, an aryloxycarbonyl group having from 7 to 32 carbon atoms, an alkylcarbonyloxy group having from 2 to 22 carbon atoms, an arylcarbonyloxy group having from 7 to 32 carbon atoms, an N-alkylsulfamoyl group having from 1 to 36 carbon atoms, an N,N-dialkylsulfamoyl group, an N-arylsulfamoyl group having from 6 to 32 carbon atoms, an N-aryl-N-alkylsulfamoyl group, an N-alkylcarbamoyl group having from 1 to 36 carbon atoms, an N,N-dialkylcarbamoyl group, an N-arylcarbamoyl group having from 6 to 32 carbon atoms, an N-aryl-N-alkylcarbamoyl group, an alkaneamido group having from 2 to 22 carbon atoms, an aromatic cyclic amido group having from 7 to 32 carbon atoms, a diacylamino group having from 3 to 32 carbon atoms, an N-alkylureido group having from 1 to 22 carbon atoms, an N,N-dialkylureido group having from 2 to 36 carbon atoms, an N-alkanesulfonamido group having from 1 to 22 carbon atoms, an N-aromatic cyclic sulfonamido group having from 6 to 32 carbon atoms, an alkylthio group having from 1 to 22 carbon atoms, an N-alkylamino group having from 1 to 32 carbon atoms, an N,N-dialkylamino group, an alkoxycarbonylamino group having from 2 to 22 carbon atoms, an aryloxycarbonylamino group having from 7 to 32 carbon atoms, an alkylsulfonyloxy group having from 1 to 22 carbon atoms, an arylsulfonyloxy group having from 6 to 32 carbon atoms, an alkylsulfonyl group having from 1 to 22 carbon atoms, a hydroxy group, and the like.

In the above formulae, $R_2$ represents hydrogen, an alkyl group (for example, a methyl group, an ethyl group, a butyl group, an octyl group, a dodecyl group, a tetradecyl group, an octadecyl group, etc.), an alkylcarbonyl group (for example, an acetyl group, a butanoyl group, an octanoyl group, a dodecanoyl group, a tetradecanoyl group, etc.), an alkoxycarbonyl group (for example, a methoxycarbonyl group, an ethoxycarbonyl group, a 2-ethylhexyloxycarbonyl group, a tetradecyloxycarbonyl group, etc.), an alkylsulfonyl group (for example, a methylsulfonyl group, an ethylsulfonyl group, an n-octylsulfonyl group, a dodecylsulfonyl group, an octadecylsulfonyl group, etc.), an N-alkylcarbamoyl group (for example, an N-methylcarbamoyl group, an N-octylcarbamoyl group, an N-hexadecylcarbamoyl group, etc.) or an N-arylcarbamoyl group (for example, a phenylcarbamoyl group, a 3-tetradecyloxyphenylcarbamoyl group, etc.).

Of these magenta color-forming couplers employed in the present invention, particularly preferred couplers are those represented by the formula (II)

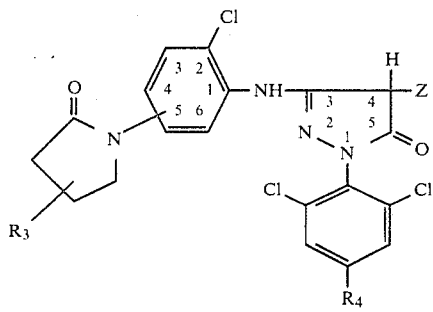

wherein Z has the same meaning as defined in formula (I), the lactam ring is present at the 4- or 5-position of the anilino ring, and $R_3$ represents hydrogen or a substituent for Y in formula (I). Of these substituents for Y, an alkyl group, an alkenyl group, an aralkyl group, an alkoxy group, an alkylthio group, an alkylsulfonyl group, an alkylcarbonyl group and an alkylcarbamoyl group are particularly preferred. $R_4$ represents a substituent which is the same as the substituents described for the 4-position of the phenyl group described above for Ar in formula (I). Hydrogen, a chlorine atom, a cyano group, an alkaneamido group, an alkanesulfonamino group, an alkoxycarbonyl group, an alkylcarbamoyl group, an alkoxycarbonylamino group, an alkylsulfonyl group or an alkylthio group is particularly preferred for $R_4$.

Couplers represented by formula (II) are particularly preferred because the spectral absorption curve of the magenta color images obtained upon color development is sharp, the second absorption zone which is characteristic of conventional pyrazolone type magenta couplers is small, and the melting point thereof is low. Furthermore, the solubility in an organic solvent having a high boiling point is high. Still further, the couplers represented by formula (II) are particularly advantageous since color images formed therefrom are light fast, and the formation of yellow stain in the unexposed areas of a color photographic element is less after color development processing upon light irradiation, and the yellow stain does not increase upon light irradiation nor with heat, as shown in the Examples hereinafter.

3-Anilino-5-pyrazolone type magenta couplers having a lactam ring or a lactam-like ring in a ballast group according to the present invention are novel couplers. Known ballast groups which having some similar structural features thereto are the N-unsubstituted acylamino group as described in U.S. Pat. No. 3,935,015 and the succinimido group as described in U.S. Pat. No. 3,684,514. However, these compounds are structurally different from the couplers according to the present invention, in which the anilino group is substituted with a lactam ring or a lactam-like ring. Also, these compounds are inferior in their photographic properties in comparison with the couplers according to the present invention, as is described in greater detail below.

The magenta-color-forming couplers according to the present invention are advantageous with respect to color reproduction in comparison with the couplers described in U.S. Pat. No. 3,935,015 in which an N-unsubstituted acylamino group is present in a ballast group, since the peak width at half height of the spectral absorption curve of the magenta dye obtained in the present invention is narrow and the hue is close to pure magenta color. Furthermore, the couplers according to the present invention are much superior to the known couplers described above in view of the good light fastness of the color images formed and the minimal amount of the formation of yellow stain at the unexposed areas after color development processing upon irradiation with light. Thus, the couplers according to the preent invention are favorable for the preparation of color light-sensitive elements, and in particular for color print light-sensitive elements.

Also, the couplers according to the present invention are favorable for the preparation of color light-sensitive elements, and, in particular, color print light-sensitive elements in comparison with the couplers described in U.S. Pat. No. 3,684,514, in which a succinimide group is present in a ballast group, because of the good light fastness of the color images formed and the small amount of the yellow stain formation at the unexposed areas after color development processing upon irradiation with light.

Specific examples of magenta color forming couplers which can be employed in the present invention are shown below, but the present invention is not to be construed as being limited thereto.

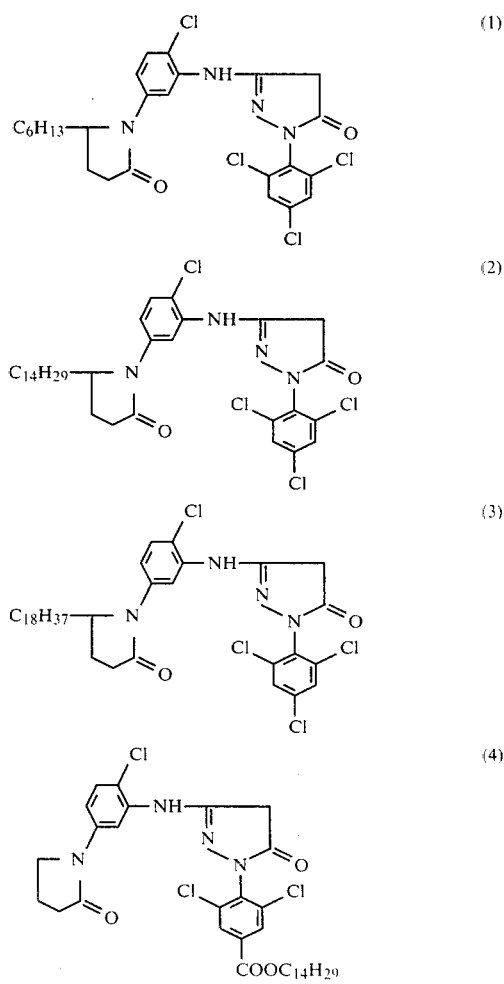

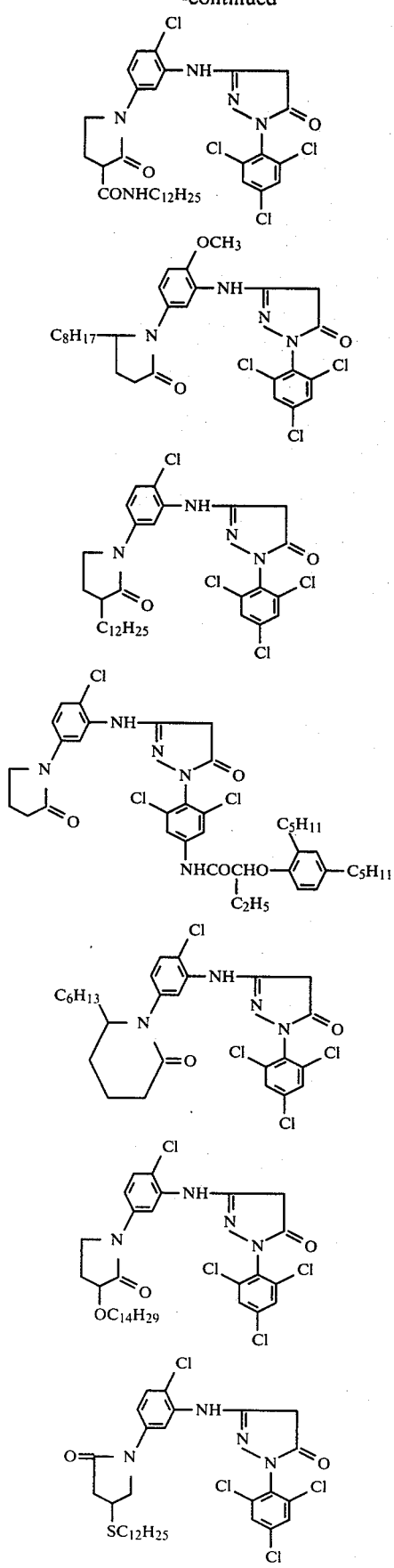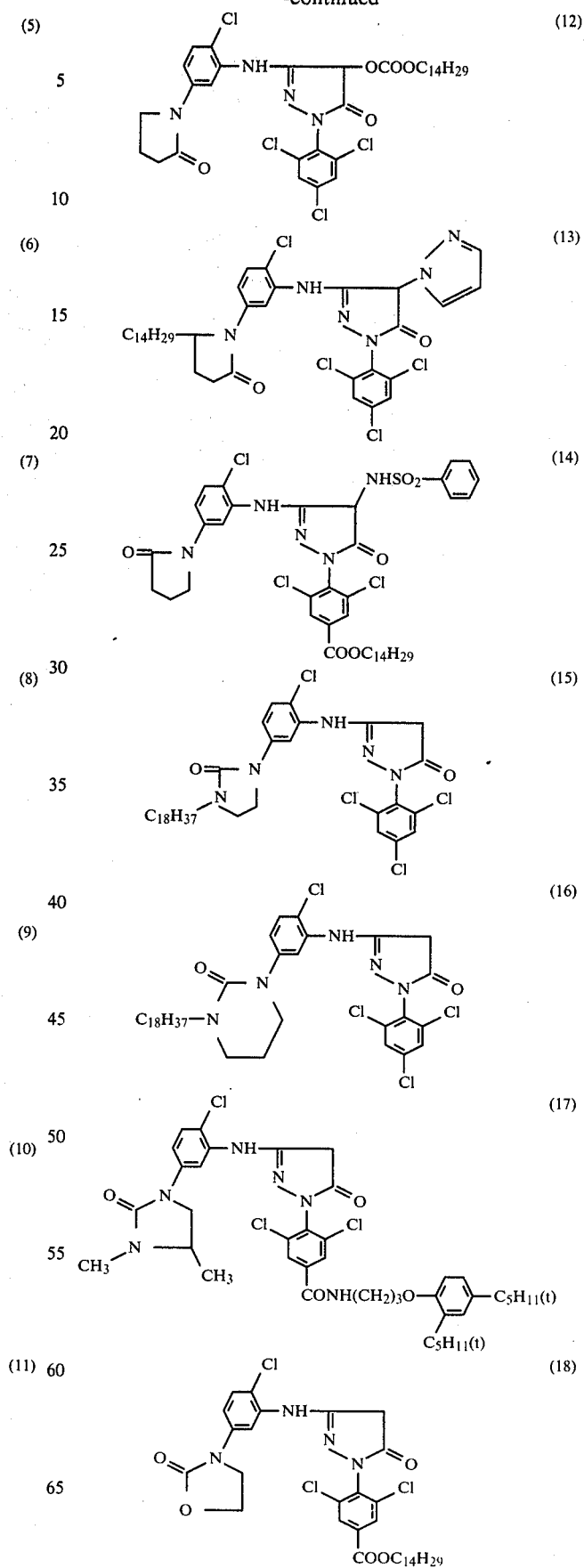

-continued

(19) 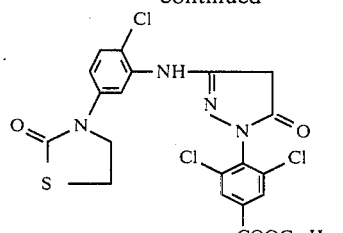

(20) 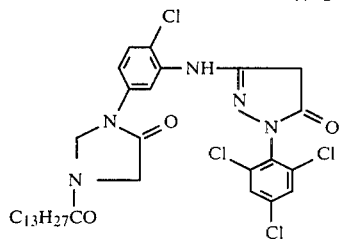

(21) 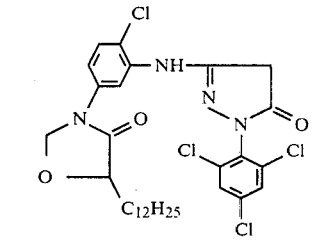

(22) 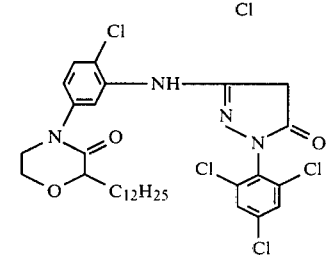

(23) 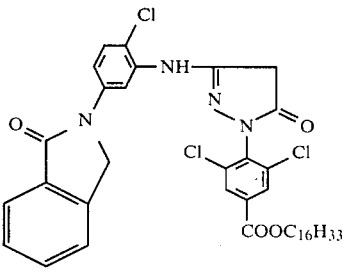

(24) 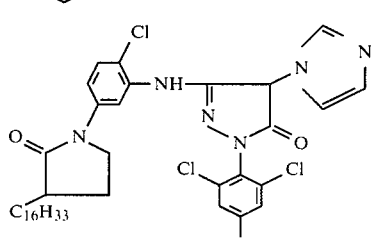

(25) 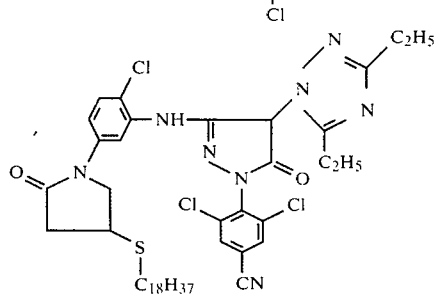

(26) 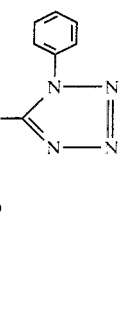

The magenta color forming coupler according to the present invention can be synthesized with known method. That is, the heterocyclic ring included in the magenta color forming coupler used in the present invention can be synthesized with reference to a method for synthesis of a corresponding heterocyclic ring. For example, the heterocyclic ring can be synthesized using the reactions:

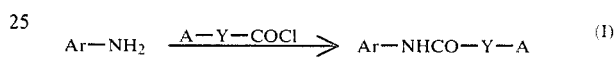

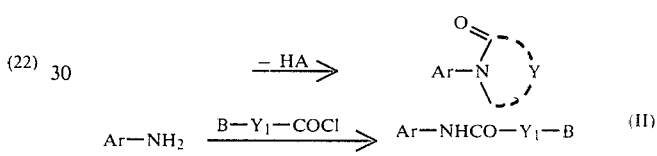

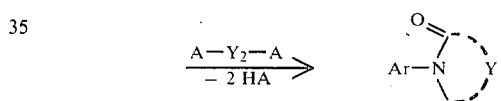

wherein Ar represents a 3-nitroaniline or a phenyl residue of a 3-anilino-2-pyrazolin-5-one coupler; Y represents a non-metallic atomic group as described above; $Y_1$ and $Y_2$ together represent the non-metallic atomic group forming Y by ring-closing; A represents a group capable of ring-closing by an elimination reaction, for example, a halogen atom (for example, a chlorine atom, a bromine atom, an iodine atom, etc.), a hydroxy group, an ester group (for example, an acetoxy group, a toluenesulfonyloxy group, etc.), and the like; and B represents a group having an active hydrogen, for example, an amino group, an acylamino group, a hydroxy group, a mercapto group, etc.

For example, as an example of the method I), the desired compound can be synthesized by the method described in Chem. Ber., Vol. 69, p. 2727 (1936), that is, by heating an aniline with a corresponding lactone compound. A 4- or 5-chloroalkylcarbonic acid chloride derivative which is easily synthesized from a lactone compound by the method described in Synthesis, p. 538 (1973) is reacted with an aniline to prepare an amide, and the latter is subjected to ring-closing using a base (for example, sodium hydride, a combination use of a quaternary ammonium salt and sodium hydroxide) to obtain the desired compound. 2-Chloroethoxycarbonyl chloride can also be used in this method. The desired compound can be synthesized by ring-closing a urea derivative, which is obtained by a reaction of an alkylisocyanate with an aniline, togerher with an alkylenedihalide (for example, 1,2-diiodoethane, etc.) and a base.

The above-described reaction is applied to a 3-nitroaniline derivative to form a heterocyclic ring followed by reduction to convert to an aniline derivative and the latter is reacted with a 3-ethoxy-2-pyrazolin-5-one derivative to prepare a 3-anilino-2-pyrazolin-5-one coupler. More preferably, the above-described reaction is applied to a 3-(3-aminoanilino)-2-pyrazolin-5-one derivative, to obtain the coupler directly.

Synthesis examples of the magenta color forming couplers which can be used in the present invention are illustrated below with reference to the specific compounds.

SYNTHESIS EXAMPLE 1

Synthesis of
3-[2-chloro-5-(2-oxo-5-hexyl-pyrrolidin-1-yl)anilino]-1-(2,4,6-trichlorophenyl)-2-pyrazolin-5-one; i.e., Coupler (1)

To 20 g of γ-decalactone, 0.5 g of anhydrous zinc chloride was added and 13 ml of thionyl chloride was dropwise added to the mixture. After stirring for 24 hours at 60° C., the reaction mixture was distilled under reduced pressure to obtain 22 g of γ-chlorodecanoyl chloride (a boiling point: 105° to 110° C./3 mmHg).

26 g of 3-(5-amino-2-chloroanilino)-1-(2,4,6-trichlorophenyl)-2-pyrazolin-5-one was suspended in 200 ml of acetonitrile and to the suspension 15.5 g of γ-chlorodecanoyl chloride described above was added dropwise under refluxing. After refluxing for 1 hour, the reaction mixture was cooled and water was added to the mixture followed by extracting with ethyl acetate. By distilling off the solvent under reduced pressure, the crystalline residue was obtained. The residue was dissolved in 300 ml of toluene; to the solution 3 g of tetrabutylammonium chloride was added, and then a solution containing 30 g of sodium hydroxide dissolved in 30 ml of water was added. After stirring vigorously at 60° C. for 4 hours, the reaction mixture was cooled and separated. The organic solvent layer was washed with water and the solvent was distilled off under reduced pressure. The residual crystals were recrystallized from acetonitrile to obtain 29 g of the desired compound. The melting point was 224° to 227° C.

Elemental Analysis: Calcd.(%): C: 53.97, H: 4.71, N: 5.04. Found (%): C: 54.02, H: 4.72, N: 5.13.

SYNTHESIS EXAMPLE 2

Synthesis of
1-(2,6-dichloro-4-tetradecyloxycarbonylphenyl)-3-[2-chloro-5-(2-oxo-pyrrolidin-1-yl)anilino]-2-pyrazolin-5-one; i.e., Coupler (4)

Step (1): Synthesis of
2-chloro-5-(2-oxo-pyrrolidin-1-yl)aniline 34.5 g of 4-chloro-3-nitroaniline was dissolved in 150 ml of acetonitrile and to the solution 33 g of γ-chlorobutyrylchloride was added under refluxing. After refluxing for 1 hour, the solvent was distilled off under reduced pressure to obtain an oily product. The oily product and 3 g of tetrabutylammonium bromide were dissolved in 150 ml of toluene and to the solution a solution containing 30 g of sodium hydroxide dissolved in 30 ml of water was added. After stirring for 30 minutes, the organic layer was separated and washed with water. By distilling off the solvent under reduced pressure, 40 g of crystalline residue was obtained.

To a mixture of the crystalline residue, 45 g of reduced iron and 3 g of ammonium chloride, 300 ml of isopropanol, and 100 ml of water were added, and the mixture was refluxed by heating with stirring for 1 hour. After removing the iron powder, water was added to the residue to deposit crystals. The crystals were collected by filtration and washed with water to obtain 32 g of the desired aniline compound. The melting point was 136° to 138° C.

Step (2): Synthesis of coupler

A mixture of 4.4 g of 2-chloro-5-(2-oxo-pyrrolidin-1-yl)aniline, 10.2 g of 1-(2,6-dichloro-4-tetradecyloxycarbonylphenyl)-3-ethoxy-2-pyrazolin-5-one and 0.5 g of methanesulfonic acid was stirred with heating at 150° C. under reduced pressure for 12 hours. After cooling, the reaction mixture was dissolved in ethyl acetate and washed three times with water. After distilling off the solvent, the residue was separated by a silica gel chromatography (using a solvent mixture of ethyl acetate and chloroform as a spreading agent) to obtain the desired compound. By recrystallization from acetonitrile 9 g of crystals having a melting point of 143° to 146° C. were obtained.

Elemental Analysis: Calcd.(%): C: 60.22, H: 6.39, N: 8.26. Found (%): C: 60.41, H: 6.42, N: 8.18.

SYNTHESIS EXAMPLE 3

Synthesis of
3-[2-chloro-5-(3-octadecylimidazolidin-2-on-1-yl)anilino]-1-(2,4,6-trichlorophenyl)-2-pyrazolin-5-one; i.e., Coupler (15)

Step (1): Synthesis of
2-chloro-5-(3-octadecylimidazolin-2-on-1-yl)aniline 17.3 g of 4-chloro-3-nitroaniline was dissolved in 200 ml of acetonitrile and to the solution 30 g of octadecyl isocyanate was added under refluxing. After refluxing for 24 hours, the reaction mixture was cooled, and the thus deposited crystals were collected by filtration to obtain 40 g of the crystals. 40 g of the crystals were added to 500 ml of toluene, and 80 g of 1,2-diiodoethane and 3 g of tetrabutylammonium bromide were added to the mixture and further a solution containing 30 g of sodium hydroxide dissolved in 30 ml of water was added. The mixture was vigorously stirred at 50° C. for 12 hours. The organic layer was washed with water and the solvent was distilled off under reduced pressure. The residue thus-obtained was refluxed for 2 hours together with 300 ml of isopropanol, 50 ml of water, 25 g of reduced iron, and 4 g of ammonium chloride. After removing the iron powder, water was added to the residue to deposit crystals. The crystals were collected by filtration and washed with water to obtain 37 g of the desired aniline compound.

Step (2): Synthesis of coupler

A mixture of 13.9 g of 2-chloro-5-(3-octadecylimidazolidin-2-on-1-yl)aniline, 9.3 g of 3-ethoxy-1-(2,4,6-trichlorophenyl)-2-pyrazolin-5-one and 1 g of methanesulfonic acid was heated at 150° C. under reduced pressure with stirring for 6 hours. After cooling, the reaction mixture was dissolved in ethyl acetate and washed three times with water. After distilling off the solvent, the residue was separated by a silica gel chromatography (using a solvent mixture of ethyl acetate and benzene as a spreading agent) to obtain the desired compound. By recrystallization from a solvent mixture of ethyl acetate and acetonitrile 10.5 g of the crystals having a melting point of 163° to 168° C. were obtained.

Elemental Analysis: Calcd.(%): C: 59.59, H: 6.81, N: 9.65. Found (%): C: 59.72, H: 6.84, N: 9.81.

The magenta color-forming coupler in accordance with the present invention possesses both high coupling activity and sufficient solubility in an organic solvent, and, therefore, a color photographic element prepared using this coupler provides photographic properties such as a good sensitivity, gradation, and the like, and possesses the characteristic that the photographic element is easy to prepare. Moreover, the color photographic element has the characteristics that not only does the photographic color image obtained by the development processing thereof possess a spectral absorption characteristic which is effective for color reproduction and sufficient light fastness, but also, after color development processing, yellow stain is reduced in the unexposed portions, and the increase in the yellow stain thereafter is minimal, even after exposure to light for a long period of time. Additionally, fading of the photographic color images due to light is significantly reduced.

Furthermore, the magenta color image obtained from the coupler in accordance with the present invention is resistant to the actions of heat and humidity. That is, the degree of color fading due to heat is serious with color images formed from 5-pyrazolones having an acylamino group or a ureido group at the 3-position thereof. This is believed to be due to the fact that the dyes formed react with the remaining coupler to produce a colorless product. For preventing color fading, a processing using a stabilizing solution containing formaldehyde or the like has been used. A characteristic of the coupler of the present invention is that dyes formed therefrom have sufficient fastness without need of such processing being necessary.

In order to prepare a silver halide color photographic light-sensitive element using the coupler of the present invention, a coupler according to the present invention can be used individually, or two or more couplers according to the present invention can be used as a mixture thereof, or a coupler according to the present invention can also be used in combination with known magenta color image-forming couplers. Further, in order to enhance the color reproduction of color photographic light-sensitive elements, magenta couplers according to the present invention can also be used in the same emulsion layer in combination with a cyan or yellow color forming coupler which has a different hue, e.g., as described in Japanese Patent Publication No. 391/65.

Pyrazolone-type compounds, indazolone type compounds, cyanoacetyl compounds, etc., can be employed as magenta color forming couplers in addition to the couplers according to the present invention, and particularly preferred couplers are pyrazolone type compounds. Specific examples of such magenta color forming couplers which can be employed are those described, for example, in U.S. Pat. Nos. 2,600,788, 2,983,608, 3,062,653, 3,127,269, 3,311,476, 3,419,391, 3,519,429, 3,558,319, 3,582,322, 3,615,506, 3,834,908 and 3,891,445, German Pat. No. 1,810,464, German patent application (OLS) Nos. 2,408,665, 2,417,945, 4,418,959 and 2,424,467, Japanese patent publication No. 6031/65, Japanese patent application (OPI) Nos. 20826/76, 58922/77, 129538/74, 74027/74, 159336/75, 42121/77, 74028/74, 60233/75, 26541/76, and 55122/78, and so forth.

Known open chain ketomethylene type couplers can be used as yellow color-forming couplers in color photographic light-sensitive element according to the present invention. Of these couplers, benzoyl acetanilide type and pivaloyl acetanilide type compounds are especially effective. Specific examples of yellow color forming couplers which can be employed are described, for example, in U.S. Pat. Nos. 2,875,057, 3,265,506, 3,408,194, 3,551,155, 3,582,322, 3,725,072 and 3,891,445, German Pat. No. 1,547,868, German patent application (OLS) Nos. 2,219,917, 2,261,361 and 2,414,006, British Pat. No. 1,425,020, Japanese patent publication No. 10783/76, Japanese patent application (OPI) Nos. 26133/72, 73147/73, 102636/76, 6341/75, 123342/75, 130442/75, 21827/76, 87650/75, 82424/77 and 115219/77, and so forth.

Phenol type compounds, naphthol type compounds, etc., can be employed as cyan color forming couplers. Specific examples of cyan color forming couplers which can be employed are those described, for example, in U.S. Pat. Nos. 2,369,929, 2,434,272, 2,474,293, 2,521,908, 2,895,826, 3,034,892, 3,311,476, 3,458,315, 3,476,563, 3,583,971, 3,591,383, 3,767,411 and 4,004,929, German patent application (OLS) Nos. 2,414,830 and 2,454,329, Japanese patent application (OPI) Nos. 59838/73, 26034/76, 5055/73, 146828/76, 69624/77 and 90932/77, and so forth.

Colored couplers which can be employed are those described, for example, in U.S. Pat. Nos. 3,476,560, 2,521,908 and 3,034,892, Japanese patent publication Nos. 2016/69, 22335/63, 11304/67 and 32461/69, Japanese patent application (OPI) Nos. 26034/76 and 42121/77, German patent application (OLS) No. 2,418,959, etc.

Development inhibitor releasing DIR couplers which can be employed are those described, for example, in U.S. Pat. Nos. 3,227,554, 3,617,291, 3,701,783, 3,790,384 and 3,632,345, German patent application (OLS) Nos. 2,414,006, 2,454,301 and 2,454,329, British Pat. No. 953,454, Japanese patent application (OPI) Nos. 69624/77, 122335/74, and Japanese patent publication No. 16141/76.

In addition to DIR couplers, other compounds which release development inhibitors upon development can also be present in the light-sensitive material. For example, those DIR compounds as described, for example, in U.S. Pat. Nos. 3,297,445 and 3,379,529, German patent application (OLS) No. 2,417,914, Japanese patent application (OPI) Nos. 15271/77 and 9116/78, etc., can be employed.

Two or more kinds of the couplers described above can be incorporated in the same layer or the same coupler compound can also be present in two or more layers.

These couplers are incorporated into the emulsion layers, generally in an amount of from about $2 \times 10^{-3}$ mol to about $5 \times 10^{-1}$ mol, preferably $1 \times 10^{-2}$ mol to $5 \times 10^{-1}$ mol, per mol of silver.

Conventional methods, e.g., the method described in U.S. Pat. No. 2,322,027, can be employed to incorporate the couplers into the silver halide emulsion layers. For example, the couplers can be dissolved in phthalic acid alkyl esters (e.g., dibutyl phthalate, dioctyl phthalate, etc.), phosphoric acid esters (e.g., diphenyl phosphate, triphenyl phosphate, tricresyl phosphate, dioctylbutyl phosphate), citric acid esters (e.g., tributyl acetylcitrate), benzoic acid esters (e.g., octyl benzoate), alkyl amides (e.g., diethyl laurylamide), fatty acid esters (e.g., dibutoxyethyl succinate, dioctyl azelate), etc.; or an organic solvent having a relatively low boiling point of from about 30° to 150° C. such as a lower alkyl acetate (e.g., ethyl acetate, butyl acetate, etc.); ethyl propionate, sec-butyl alcohol, methyl isobutyl ketone, β-ethoxyethyl acetate, methyl Cellosolve acetate. Then the solution is dispersed in a hydrophilic colloid. The above-described organic solvents having a high boiling point and the above-described organic solvents having a low boiling point may be used as mixtures, if desired.

Furthermore, the dispersing method using a polymeric material as described in Japanese patent publication No. 39853/76, Japanese patent application (OPI) No. 59943/76 can also be used.

When couplers having an acid group such as a carboxylic acid group, a sulfonic acid group, etc., are used, they can be incorporated in a hydrophilic colloid as an alkaline aqueous solution thereof.

The photographic emulsion used in this invention can be prepared using the methods described in, e.g., P. Glafkides, *Chimie-et Physique Photographique*, Paul Montel, Paris (1967), G. F. Duffin, *Photographic Emulsion Chemistry*, The Focal Press, London (1966), V. L. Zelikman, et al., *Making and Coating Photographic Emulsions*, The Focal Press, London (1964), etc. That is, any of the acid method, the neutral method, the ammonia method and other methods can be used. Moreover, a soluble silver salt can be reacted with a soluble halogen salt using any of the single jet method, the double jet method and a combination thereof.

A method in which grains are formed in the presence of an excess of silver ions (i.e., the so-called reverse mixing method) can also be used. As one of the modes of the double jet method, the method in which the pAg of the liquid phase in which the silver halide is to be produced is kept constant, that is, the so-called controlled double jet method, can be used. This method can provide silver halide emulsions having a regular crystal form and an almost uniform grain size.

Two or more silver halide emulsions which are separately prepared can be mixed and then used, if desired.

In the process of the formation of the silver halide grains or physical ripening, cadmium salts, zinc salts, lead salts, thallium salts, iridium salts or complex salts thereof, rhodium salts or complex salts thereof, iron salts or iron complex salts, and the like can be present.

Gelatin can advantageously be used as the binder or protective colloid for the photographic emulsion used in this invention. However, other hydrophilic colloids can be used as well. For example, proteins such as gelatin derivatives, graft polymers between gelatin and other high polymers, albumin, casein, etc.; cellulose derivatives such as hydroxyethyl cellulose, carboxymethyl cellulose, cellulose sulfates, etc.; saccharide derivatives such as sodium alginate, starch derivatives, etc.; and various synthetic hydrophilic high polymers of monoor copolymers such as polyvinyl alcohol, polyvinyl alcohol partial acetal, poly-N-vinylpyrrolidone, polyacrylic acid, polymethacrylic acid, polyacrylamide, polyvinylimidazole, polyvinylpyrazole, etc., can be used as the binder or protective colloid for the photographic emulsion.

Acid-processed gelatin and enzyme-processed gelatin as described in *Bull. Soc. Sci. Photo. Japan*, No. 16, p. 30 (1966) can be used as well as lime-processed gelatin as the gelatin component. In addition, the hydrolyzed products of gelatin and enzyme-decomposed products of gelatin are also suitable. Suitable gelatin derivatives which can be used include those obtained by reacting gelatin with various compounds, such as acid halides, acid anhydrides, isocyanates, bromoacetic acid, alkanesultones, vinylsulfonamides, maleinimides, polyalkylene oxides, epoxy compounds, etc. Specific examples thereof are described in U.S. Pat. Nos. 2,614,928, 3,132,945, 3,186,846, 3,312,533, British Pat. Nos. 861,414, 1,033,189, 1,005,784, Japanese patent publication No. 26845/67.

As the above-described gelatin graft polymer, those which are obtained by grafting homo- or copolymers of vinyl monomers such as acrylic acid, methacrylic acid, the ester or amide derivatives thereof, acrylonitrile, styrene, etc., to gelatin can be used. In particular, graft polymers with a polymer having some compatibility with gelatin, such as polymers of acrylic acid, methacrylic acid, acrylamide, methacrylamide, hydroxyalkyl methacrylates, etc., are preferred. Examples thereof are described in U.S. Pat. Nos. 2,763,625, 2,831,767, 2,956,884, etc. Typical synthetic hydrophilic materials are described in, e.g., German patent application (OLS) No. 2,312,708, U.S. Pat. Nos. 3,620,751, 3,879,205 and Japanese patent publication No. 7561/68.

For the purposes of preventing fog or stabilizing the photographic properties during preparation, storage, and/or during photographic processing of light-sensitive materials, a variety of compounds can be incorporated into photographic emulsions used according to the present invention. For example, a wide variety of compounds which are known as anti-fogging agents or stabilizers, such as azoles, e.g., benzothiazolium salts, nitrobenzimidazoles, nitroindazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles (especially 1-phenyl-5-mercaptotetrazole), etc.; mercaptopyrimidines; mercaptotriazines; thio keto compounds, such as oxazolinethione; azaindenes, e.g., triazaindenes, tetrazaindenes (especially 4-hydroxy-substituted (1,3,3a,7-)tetrazaindene), pentazaindenes, etc.; benzenethiosulfonic acid, benzenesulfinic acid, benzenesulfonic amide, etc., can be used. For example, the compounds as described in U.S. Pat. Nos. 3,954,474 and 3,982,947, Japanese patent publication No. 28660/77 can be used.

For the purpose of increasing sensitivity, increasing contrast or accelerating development, photographic emulsion layer of the photographic light-sensitive element according to the present invention can contain other known additives, such as, for example, polyalkylene oxides or derivatives thereof such as ethers, esters, amines, etc., thioether compounds, thiomorpholine compounds, quaternary ammonium compounds, urethane derivatives, urea derivatives, imidazole derivatives, 3-pyrazolidones, etc. For example, such additives as described in U.S. Pat. Nos. 2,400,532, 2,423,549, 2,716,062, 3,617,280, 3,772,021, 3,808,003, British Pat. No. 1,488,991, etc.

The photographic emulsion layers and other hydrophilic colloid layers of the light-sensitive material prepared in accordance with the present invention can contain whitening agents such as stilbenes, triazines, oxazoles, or coumarins, etc. These agents can be water-soluble or can also be employed as a dispersion of water-insoluble whitening agents. Specific examples of fluorescent whitening agents are described in U.S. Pat. Nos. 2,632,701, 3,269,840 and 3,359,102, and British Pat. Nos. 852,075 and 1,319,763.

The hydrophilic colloid layers of the lightsensitive material prepared according to the present invention can contain water-soluble dyes such as filter dyes or for various purposes of preventing irradiation or other purposes. Such dyes include oxonol dyes, hemioxonol dyes, styryl dyes, merocyanine dyes, cyanine dyes and azo dyes. Of these dyes, oxonol dyes, hemioxonol dyes and merocyanine dyes are especially useful. Specific examples of dyes which can be employed are described, for example, in British Pat. Nos. 584,609 and 1,177,429, Japanese patent application (OPI) Nos. 85130/73, 99620/74, 114420/74 and 108115/77, and U.S. Pat. Nos. 2,274,782, 2,533,472, 2,956,879, 3,148,187, 3,177,078, 3,247,127, 3,540,887, 3,575,704, 3,653,905, 3,718,472, 4,071,312, and 4,070,352.

The photographic emulsion of the present invention can also be spectrally sensitized with methine dyes or other dyes. Suitable dyes which can be employed include cyanine dyes, merocyanine dyes, complex cyanine dyes, complex merocyanine dyes, holopolar cyanine dyes, hemicyanine dyes, styryl dyes, and hemioxonol dyes. Of these dyes, cyanine dyes, merocyanine dyes and complex merocyanine dyes are particularly useful. Any conventionally utilized nucleus for cyanine dyes such as basic heterocyclic nuclei is applicable to these dyes. That is, a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, a pyridine nucleus, etc., and further, nuclei formed by fusing alicyclic hydrocarbon rings with these nuclei and nuclei formed by condensing aromatic hydrocarbon rings with these nuclei, that is, an indolenine nucleus, a benzindolenine nucleus, an indole nucleus, a benzoxazole nucleus, a naphthoxazole nucleus, a benzothiazole nucleus, a naphthothiazole nucleus, a benzoselenazole nucleus, a benzimidazole nucleus, a quinoline nucleus, etc., are appropriate. The carbon atoms of these nuclei can also be substituted.

Among merocyanine dyes that can be employed are complex merocyanine dyes containing 5- or 6-membered heterocyclic nuclei such as a pyrazolin-5-one nucleus, a thiohydantoin nucleus, a 2-thioxazolidin-2,4-dione nucleus, a thiazolidin-2,4-dione nucleus, a rhodanine nucleus, a thiobarbituric acid nucleus, and so forth.

Useful sensitizing dyes include those described in German Pat. No. 929,080, U.S. Pat. Nos. 2,231,658, 2,493,748, 2,503,776, 2,519,001, 2,912,329, 3,656,959, 3,672,897, 3,694,217, 4,025,349 and 4,046,572, British Pat. No. 1,242,588, Japanese patent publication Nos. 14030/69 and 24844/77, and so forth.

These sensitizing dyes can be employed individually, and can also be employed in combination. A combination of sensitizing dyes is often used particularly for the purpose of supersensitization.

Representative examples thereof are described in U.S. Pat. Nos. 2,688,545, 2,977,229, 3,397,060, 3,522,052, 3,527,641, 3,617,293, 3,628,964, 3,666,480, 3,672,898, 3,679,428, 3,703,377, 3,769,301, 3,814,609, 3,837,862 and 4,026,707, British Pat. Nos. 1,344,281, and 1,507,803, Japanese patent publication Nos. 4936/68 and 12375/78, and Japanese patent application (OPI) Nos. 110618/77 and 109925/77.

The sensitizing dyes may be present in the emulsion together with dyes which themselves do not give rise to spectrally sensitizing effects but exhibit a supersensitizing effect or materials which do not substantially absorb visible light but exhibit a supersensitizing effect. For example, aminostilbene compounds substituted with a nitrogen-containing heterocyclic ring group (e.g., those described in U.S. Pat. Nos. 2,933,390 and 3,635,721), aromatic organic acid-formaldehyde condensates (e.g., those described in U.S. Pat. No. 3,743,510), cadmium salts, azaindene compounds, and the like, can be present. The combinations described in U.S. Pat. Nos. 3,615,613, 3,615,641, 3,617,295 and 3,635,721 are particularly useful.

The present invention is also applicable to multilayer multicolor photographic materials containing layers sensitive to at least two different spectral wavelength ranges on a support. A multilayer color photographic material generally possesses at least one red-sensitive silver halide emulsion layer, at least one green-sensitive silver halide emulsion layer and at least one blue-sensitive silver halide emulsion layer, respectively, on a support. The order of these layers can be varied optionally as desired. Ordinarily, a cyan forming coupler is present in a red-sensitive emulsion layer, a magenta forming coupler is present in a green-sensitive emulsion layer and a yellow forming coupler is present in a blue-sensitive emulsion layer, respectively. However, if desired, a different combination can be employed.

Light-sensitive elements prepared according to the present invention can also contain, as color fog preventing agents, hydroquinone derivatives, aminophenol derivatives, gallic acid derivatives, ascorbic acid derivatives, or the like. Specific examples of these agents are described in U.S. Pat. Nos. 2,360,290, 2,336,327, 2,403,721, 2,418,613, 2,675,314, 2,701,197, 2,704,713, 2,728,659, 2,732,300 and 2,735,765, Japanese patent application (OPI) Nos. 92988/75, 92989/75, 93928/75, 110337/75 and 146235/77, Japanese patent publication No. 23813/75, and so forth.

The hydrophilic colloid layers of the light-sensitive elements prepared in accordance with the present invention can also contain UV absorbents. For example, benzotriazole compounds substituted with aryl groups (e.g., those described in U.S. Pat. No. 3,533,794), 4-thiazolidone compounds (e.g., those described in U.S. Pat. Nos. 3,314,794 and 3,352,681), benzophenone compounds (e.g., those described in Japanese patent application (OPI) No. 2784/71), cinnamic acid ester compounds (e.g., those described in U.S. Pat. Nos. 3,707,375 and 3,705,805), butadiene compounds (e.g., those described in U.S. Pat. No. 4,045,229) or benzoxazole compounds (e.g., those described in U.S. Pat. No. 3,700,455) can be employed. Furthermore, the compounds as described in U.S. Pat. No. 3,499,762, Japanese patent application (OPI) No. 48535/79 can also be used. UV absorbing couplers (e.g., α-naphthol type cyan color forming couplers) and UV absorbing polymers can also be employed. These UV absorbents can also be mordanted in a specific layer(s), if desired.

In the practice of the present invention, known color fading preventing agents as described below can be employed. These fading preventing agents can be used individually or in a combination of two or more thereof. Specific examples of known color fading preventing agents include, for example, hydroquinone derivatives as described in U.S. Pat. Nos. 2,360,290, 2,418,613, 2,675,314, 2,701,197, 2,704,713, 2,728,659, 2,732,300, 2,735,765, 2,710,801 and 2,816,028, British Pat. No. 1,363,921; gallic acid derivatives as described in U.S. Pat. Nos. 3,457,079 and 3,069,262; p-alkoxyphenols as described in U.S. Pat. Nos. 2,735,765 and 3,698,909, Japanese patent publication Nos. 20977/74 and 6623/77; p-oxyphenol derivatives as described in U.S. Pat. Nos. 3,432,300, 3,573,050, 3,574,627 and 3,764,337, Japanese patent application (OPI) Nos. 35633/77, 147434/77 and 152225/77; bisphenol derivatives as described in U.S. Pat. No. 3,700,455, etc.

Known methods can be used for processing the light-sensitive material according to the present invention. Known processing solutions can be used. The processing temperature can be between about 18° C. and about 50° C., in general, but temperatures lower than about 18° C. or higher than about 50° C. may be used, if desired. Either a development processing for forming silver images (black-and-white photographic processing) or a color photographic processing comprising developing processing for forming dye images can be employed, as desired.

Among methods that can be employed are a negative-positive method (for example, as described in *Journal of the Society of Motion Picture and Television Engineers*, Vol. 61, pp. 667–701 (1953)); a color reversal method which comprises developing with a developer containing a black-and-white developing agent to form a negative silver image, then subjecting the photographic material to at least one uniform exposure or to another appropriate fogging treatment, and subsequently performing color development to obtain positive dye images; and a silver dye bleaching method which comprises exposing a dye-containing photographic emulsion layer and developing the same to form a silver image and then bleaching the dyes using the silver image as a bleaching catalyst.

The color developer generally comprises an alkaline aqueous solution containing a color developing agent. Suitable color developing agents which can be employed include known primary aromatic amine developing agents, e.g., phenylenediamines (e.g., 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 3-methyl-4-amino-N-ethyl-N-β-methanesulfamidoethylaniline, 4-amino-3-methyl-N-ethyl-N-β-methoxyethylaniline, etc.).

In addition, those developing agents described in L. F. A. Mason, *Photographic Processing Chemistry*, at pages 226 to 229, Focal Press (1966), U.S. Pat. Nos. 2,193,015 and 2,592,364, Japanese patent application (OPI) No. 64933/73, etc., can be employed.

The color developers can also contain pH buffering agents such as sulfites, carbonates, borates and phosphates of alkali metals, developing inhibitors or anti-fogging agents such as bromides, iodides or organic anti-fogging agents, etc. In addition, if desired, the color developers can also contain water softeners, preservatives such as hydroxylamine; organic solvents such as benzyl alcohol, diethylene glycol, etc.; developing accelerators such as polyethylene glycol, quaternary ammonium salts, amines; dye forming couplers; competing couplers; fogging agents such as sodium borohydride; auxiliary developers such as 1-phenyl-3-pyrazolidone; viscosity-imparting agents; polycarboxylic acid type chelating agents described in U.S. Pat. No. 4,083,723; antioxidizing agents as described in German patent application (OLS) No. 2,622,950; and the like.

The photographic emulsion layers after color development are generally bleach-processed. Bleach processing can be performed at the same time as fixing or separately therefrom. Suitable bleaching agents which can be employed are compounds of polyvalent metals such as iron (III), cobalt (III), chromium (VI), copper (II), etc., peracids, quinones, nitroso compounds, etc. Specific examples include ferricyanides; bichromates; organic complexes of iron (III) or cobalt (III); aminopolycarboxylic acids such as ethylenediaminetetraacetic acid, nitrilotriacetic acid, 1,3-diamino-2-propanol tetraacetic acid, etc.; complexes of organic acids such as citric acid, tartaric acid, malic acid, etc.; persulfates; permanganates; nitrosophenol; etc. Of these, particularly useful bleaching agents are potassium ferricyanide, sodium ethylenediaminetetraacetate iron (III) and ammonium ethylenediaminetetraacetate iron (III). Ethylenediaminetetraacetate iron (III) complex is useful both in a bleaching solution and in a mono bath bleach-fixing solution.

Bleaching and bleach-fixing solutions can contain various additives including bleach accelerating agents as described in U.S. Pat. Nos. 3,042,520 and 3,241,966, Japanese patent publication Nos. 8506/70 and 8836/70, thiol compounds as described in Japanese patent application (OPI) No. 65732/78, and the like.

The characteristics obtained by employing the magenta coupler according to the present invention are more specifically explained below by reference to some specific examples. For comparison, the magenta couplers indicated below were used.

Comparison Coupler (a)

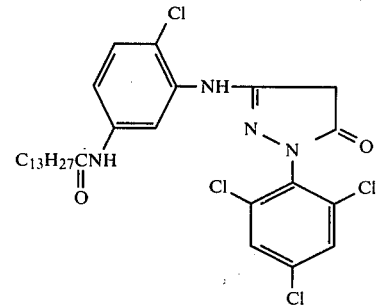

Comparison Coupler (b)

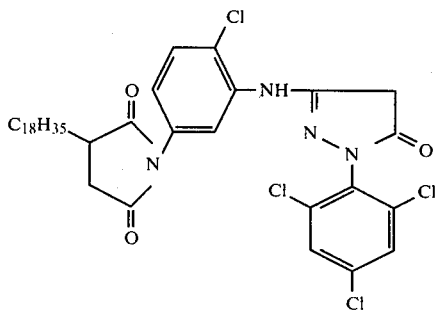

Comparison Coupler (c)

-continued

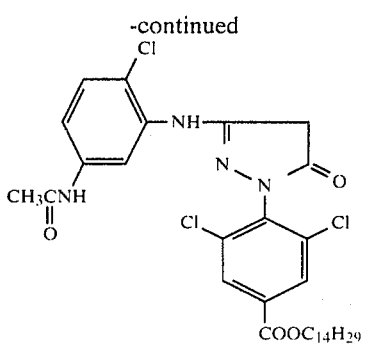

The Comparison Couplers (a) and (c) described above are described in U.S. Pat. No. 3,935,015 and the Comparison Coupler (b) described above is described in U.S. Pat. No. 3,684,514.

With Comparison Couplers (a), (b) and (c) indicated above and with Couplers (1), (3), (4), (10), (15) and (23) according to the present invention, the spectral absorption characteristics of the azomethine dye formed by the oxidation coupling reaction with 4-[N-ethyl-N-($\beta$-methanesulfonamidoethyl)]amino-2-methylaniline were measured in ethyl acetate and compared.

From the spectral absorption curves obtained, the density of a second absorption appearing in the blue light region, when the color density of the main wavelength was adjusted to 1.00, the density at a longer wavelength of 60 m$\mu$ from the main wavelength and the width of the wavelength at which the color density became 0.50 were determined. The results obtained are shown in Table 1 below.

TABLE 1

| | Peak of Main Wavelength (m$\mu$) | Color Density of Second Absorption | Color Density at 60 m$\mu$Longer Wavelength | Width of Wavelength Having Density of 0.5 |
|---|---|---|---|---|
| Coupler (1) Present Invention | 530 | 0.136 | 0.127 | 65 |
| Coupler (3) Present Invention | 529 | 0.137 | 0.127 | 66 |
| Coupler (4) Present Invention | 530 | 0.136 | 0.128 | 66 |
| Coupler (10) Present Invention | 529 | 0.138 | 0.126 | 65 |
| Coupler (15) Present Invention | 528 | 0.139 | 0.128 | 66 |
| Coupler (23) Present Invention | 530 | 0.136 | 0.128 | 66 |
| Comparison Coupler (a) | 529 | 0.141 | 0.134 | 67 |
| Comparison Coupler (b) | 527 | 0.144 | 0.131 | 69 |
| Comparison Coupler (c) | 530 | 0.140 | 0.132 | 68 |

The color images obtained using the couplers of the present invention have a sharp cut off at the long wavelength side of the peak, and undesired second absorption is minimal.

The characteristics obtained using the magenta coupler according to the present invention are explained further by reference to the examples hereinbelow.

EXAMPLE 1

10 g of Coupler (1) of the present invention was dissolved in 10 ml of tricresyl phosphate and 10 ml of ethyl acetate and the solution was dispersed in 80 g of a 10% aqueous gelatin solution containing sodium dodecylbenzenesulfonate. Thus-prepared dispersion was mixed with 145 g of a green-sensitive silver chlorobromide emulsion (50 mol% silver bromide) containing 7 g of silver, and sodium dodecylbenzenesulfonate was added thereto as a coating aid. The mixture was coated on a paper support, both surfaces of which were laminated with polyethylene. Further, to this layer a gelatin protective layer (1 g/m$^2$) was applied and dried (Sample A).

Samples (B) to (I) were prepared in a manner similar to the preparation of Sample (A) except that Couplers (3), (4), (10), (15) and (23) of the present invention and Comparison Magenta Color Image Forming Couplers (a), (b) and (c) were employed, respectively.

These samples were exposed to light of 1,000 lux.1 sec. using a sensitometer and processed with the following color developer solution.

| Color Developer Solution | |
|---|---|
| Benzyl Alcohol | 15 ml |
| Diethylene Glycol | 8 ml |
| Ethylenediaminetetraacetic Acid | 5 g |
| Sodium Sulfite | 2 g |
| Anhydrous Potassium Carbonate | 30 g |
| Hydroxylamine Sulfate | 3 g |
| Potassium Bromide | 0.6 g |
| 4-Amino-N-ethyl-N-($\beta$-methanesulfonamidoethyl)-m-toluidine Sesquisulfate Monohydrate | 5 g |
| Adjust pH to 10.20 | |
| Water to make | 1 l |
| Bleach-Fixing Solution | |
| Ethylenediaminetetraacetic Acid | 2 g |
| Ferric Salt of Ethylenediaminetetraacetate | 40 g |
| Sodium Sulfite | 5 g |
| Ammonium Thiosulfate | 70 g |
| Water to make | 1 l |

| Processing Step | Temperature (°C.) | Time |
|---|---|---|
| 1. Color development | 33 | 3 min 30 sec |
| 2. Bleach-fixing | 33 | 1 min 30 sec |
| 4. Washing with water | 25 to 30 | 2 min 30 sec |

Each sample thus-processed to form a dye image was subjected to fading testing for 2 weeks using a fluorescent lamp fading tester (20,000 lux) equipped with an ultraviolet light absorbing filter capable of absorbing substantially all ultraviolet lights having a wavelength of 400 m$\mu$ or less (manufactured by Fuji Photo Film Co., Ltd.). The results obtained are shown in Table 2 below.

TABLE 2

| Sample No. | Coupler Used | Change of Yellow Stain Density in White Background* | Change of Magenta Density (initial density of 1.0) |
|---|---|---|---|
| A | Coupler (1) Present Invention | +0.08 | −0.30 |
| B | Coupler (3) Present Invention | +0.07 | −0.26 |
| C | Coupler (4) Present Invention | +0.10 | −0.28 |
| D | Coupler (10) Present Invention | +0.07 | −0.25 |
| E | Coupler (15) Present Invention | +0.08 | −0.35 |
| F | Coupler (23) Present Invention | +0.09 | −0.31 |
| G | Comparison Coupler (a) | +0.17 | −0.53 |
| H | Comparison Coupler (b) | +0.14 | −0.47 |
| I | Comparison Coupler (c) | +0.20 | −0.56 |

*The yellow density in white background before the fading test was 0.10.

It is apparent from the results in Table 2 above that couplers according to the present invention provide less formation of yellow stain in white background upon irradiation with light and also less fading of the color image upon irradiation with light.

EXAMPLE 2

On a paper support both surfaces of which were laminated with polyethylene were coated a first layer (undermost layer) to a sixth layer (uppermost layer) as shown in Table 3 in order to prepare a color light-sensitive material. A coating composition for a third layer was prepared in accordance with the procedure as described in Example 1, except for the addition of the color image stabilizer. The samples thus prepared were designated corresponding to the couplers employed as shown in Table 4.

These samples were exposed using a sensitometer to light of 1,000 lux·1 sec equipped with a green filter, SP-2 (made by Fiji Photo Film Co., Ltd.). Then, these samples were subjected to the same processing as described in Example 1.

Each sample having a dye image thus-formed was subjected to fading testing for 4 weeks using a fluorescent lamp fading tester (20,000 lux). The results obtained are shown in Table 4 below.

Color Image Stabilizer (d)

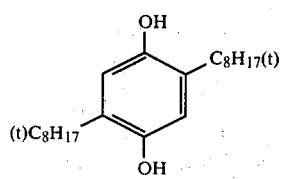

Color Image Stabilizer (e)

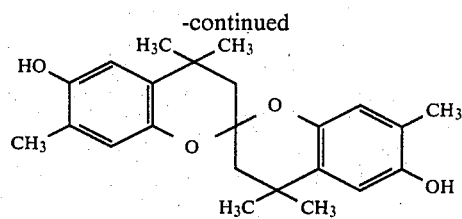

TABLE 3

| | |
|---|---|
| Sixth Layer: (protective layer) | Gelatin (1,000 mg/m²) |
| Fifth Layer: (red-sensitive layer) | Silver chlorobromide emulsion (Br: 50 mol %), Silver (300 mg/m²), Gelatin (1,000 mg/m²), Cyan coupler*¹ (400 mg/m²), Coupler solvent*² (200 mg/m²) |
| Fourth Layer: (interlayer) | Gelatin (1,200 mg/m²), Ultraviolet light-absorbing agent*³ (1,000 mg/m²), Ultraviolet light-absorbing agent solvent*² (250 mg/m²) |
| Third Layer: (green-sensitive layer) | Silver chlorobromide emulsion (Br: 50 mol%), Silver (290 mg/m²), Gelatin (1,000 mg/m²), Magenta coupler (200 mg/m²), Coupler solvent*⁴ (200 mg/m²) |
| Second Layer: (interlayer) | Gelatin (1,000 mg/m²) |
| First Layer: (blue-sensitive layer) | Silver chlorobromide emulsion (Br: 80 mol %), Silver (400 mg/m²), Gelatin (1,200 mg/m²), Yellow coupler*⁵ (300 mg/m²), Coupler solvent*⁶ (150 mg/m²) |
| Support: | Paper support both surfaces of which were laminated with polyethylene |

*¹Coupler: 2-[α-(2,4-Di-tert-pentylphenoxy)butanamido]-4,6-dichloro-5-methylphenol
*²Solvent: Dibutyl phthalate
*³Ultraviolet light-absorbing agent: 2-(2-Hydroxy-3-sec-butyl-5-tert-butylphenyl)-benzotriazole
*⁴Solvent: Tricresyl phosphate
*⁵Coupler: α-Pivaloyl-α-[2,4-dioxo-5-5'-dimethyloxyazolidin-3-yl]-2-chloro-5-[α-(2,4-di-tert-pentylphenoxy)butanamido]acetanilide
*⁶Solvent: Dioctyl butyl phosphate

TABLE 4

| Sample No. | Couplers and Color Image Stabilizers Used | Change of Yellow Stain Density in White Background* | Change of Magenta Density (initial density of 0.1) |
|---|---|---|---|
| J | Coupler (3) Present Invention Color Image Stabilizer (d) Color Image Stabilizer (e) | +0.05 | −0.21 |
| K | Coupler (10) Present Invention Color Image Stabilizer (d) Color Image Stabilizer (e) Comparison Coupler (a) | +0.06 | −0.26 |
| L | Color Image Stabilizer (d) Color Image Stabilizer (e) Comparison Coupler (b) | +0.15 | −0.39 |
| M | Color Image Stabilizer (d) Color Image Stabilizer (e) | +0.13 | −0.40 |

*The Yellow density in white background before the fading test was 0.10.

It is apparent from the results in Table 4 above that couplers according to the present invention provide less formation of yellow stain in white background upon irradiation with light and also less fading of the color image upon irradiation with light.

While the invention has been described in detail and with reference to specific embodiments thereof, it will be apparent to one skilled in the art that various changes and modifications can be made therein without departing from the spirit and scope thereof.

What is claimed is:

1. A color photographic light-sensitive element comprising a support having thereon a silver halide emulsion layer containing therein a 3-anilino-5-pyrazolone magenta color forming coupler represented by formula (I)

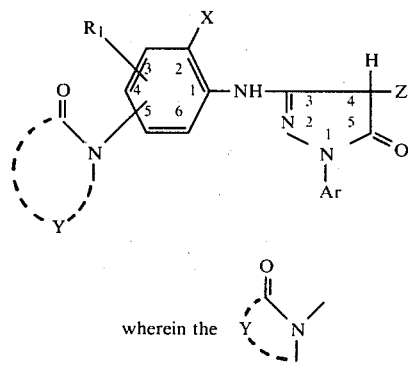

wherein the 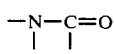

is present at the 4- or 5-position of the anilino group; X represents a halogen atom or an alkoxy group; Ar represents an aryl group; $R_1$ represents hydrogen, a halogen atom, an alkyl group, an alkoxy group, or an alkylthio group; Y represents a non-metallic atomic group forming a 5-membered or 6-membered ring together with the $$-N-C=O$$
$$\phantom{-N-}|\phantom{-}|$$

group, except that Y does not include a carbonyl group; and Z represents hydrogen or a coupling-off group.

2. A color photographic light-sensitive element as in claim 1, wherein X represents a chlorine atom, a bromine atom, or an alkoxy group having from 1 to 22 carbon atoms, which may be substituted with one or more substituents selected from a halogen atom, a nitro group, a cyano group, an alkoxy group, an aryloxy group, an alkylcarbonyl group, an alkoxycarbonyl group, an acylamine group, a sulfonamido group, a hydroxy group, and a mercapto group.

3. A color photographic light-sensitive element as in claim 1, wherein Z represents hydrogen.

4. A color photographic light-sensitive element as in claim 1, wherein Z represents a coupling-off group.

5. A color photographic light-sensitive element as in claim 1, wherein Z represents hydrogen, a thiocyano group, an acyloxy group, an aryloxy group, an alkoxy group, a halogen atom, an arylazo group, an aryltriazolyl group, an alkylthio group, an arylthio group, a heterocyclic thio group, an aralkoxycarbonyloxy group, an alkoxycarbonyloxy group, an aryloxycarbonyloxy group, a cycloalkylthio group, a cycloalkoxy group, an imido group, an imidazolyl group, a pyrazolyl group, a triazolyl group, an acylamino group, a sulfonamido group or a cycloamino group.

6. A color photographic light-sensitive element as in claim 1, wherein Ar represents a phenyl group which may be substituted with one or more substituents selected from a halogen atom, a cyano group, an alkyl group, an alkoxy group, an acylamino group, a sulfamoyl group, a sulfonamido group, an alkoxycarbonyl group, an alkylthio group, an alkylsulfonyl group, a carbamoyl group, a nitro group and a trifluoromethyl group.

7. A color photographic light-sensitive element as in claim 1, wherein the nucleus represented by the formula of

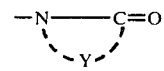

is selected from the group consisting of

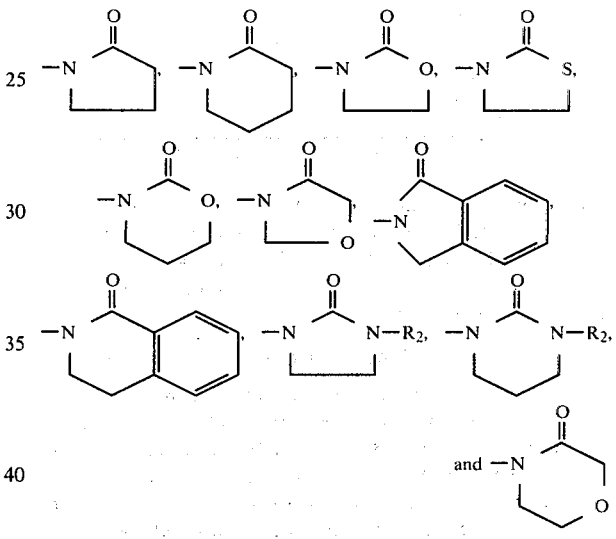

wherein $R_2$ represents hydrogen, an alkyl group, an alkylcarbonyl group, an alkoxycarbonyl group, an alkylsulfonyl group, an N-alkylcarbamoyl group, or an N-arylcarbamoyl group.

8. A color photographic light-sensitive element as in claim 1, wherein said 5- or 6-membered ring may be substituted with one or more substituents selected from a straight chain or branched chain alkyl group having from 1 to 22 carbon atoms, an alkenyl group, a cycloalkyl group, a cycloalkenyl group, an aralkyl group having from 7 to 32 carbon atoms, a carboxy group, an alkoxy group having from 1 to 22 carbon atoms, a halogen atom, a cyano group, an aryl group having from 6 to 32 carbon atoms, an alkylcarbonyl group having from 2 to 22 carbon atoms, an arylcarbonyl group having from 7 to 32 carbon atoms, an alkoxycarbonyl group having from 2 to 22 carbon atoms, an aryloxycarbonyl group having from 7 to 32 carbon atoms, an alkylcarbonyloxy group having from 2 to 22 carbon atoms, an arylcarbonyloxy group having from 7 to 32 carbon atoms, an N-alkylsulfamoyl group having from 1 to 36 carbon atoms, an N,N-dialkylsulfamoyl group, an N-arylsulfamoyl group having from 6 to 32 carbon atoms, an N-aryl-N-alkylsulfamoyl group, an N-alkylcarbamoyl group having from 1 to 36 carbon atoms, an N,N- dialkylcarbamoyl group, an N-arylcarbamoyl group having from 6 to 32 carbon atoms, an N-aryl-N-alkylcarbamoyl group, an alkaneamido group having from 2 to 22 carbon atoms, an aromatic cyclic amido group having from 7 to 32 carbon atoms, a diacylamino group having from 3 to 32 carbon atoms, an N-alkylureido group having from 1 to 22 carbon atoms, an N,N-dialkylureido group having from 2 to 36 carbon atoms, an N-alkanesulfonamido group having from 1 to 22 carbon atoms, an N-aromatic cyclic sulfonamido group having from 6 to 32 carbon atoms, an alkylthio group having from 1 to 22 carbon atoms, an N-alkylamino group having from 1 to 32 carbon atoms, an N,N-dialkylamino group, an alkoxycarbonylamino group having from 2 to 22 carbon atoms, an aryloxycarbonylamino group having from 7 to 32 carbon atoms, an alkylsulfonyloxy group having from 1 to 22 carbon atoms, an arylsulfonyloxy group having from 6 to 32 carbon atoms, an alkylsulfonyl group having from 1 to 22 carbon atoms, and a hydroxy group.

9. A color photographic light-sensitive element as in claim 1, wherein said magenta color-forming coupler is represented by formula (II)

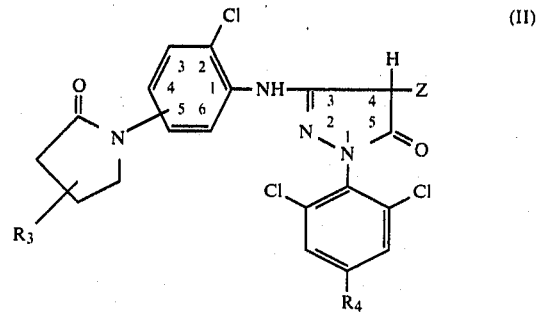

wherein Z represents hydrogen or a coupling-off group; the lactam ring is present at the 4- or 5-position of the anilino group; $R_3$ represents hydrogen, an alkyl group, an alkenyl group, an aralkyl group, an alkoxy group, an alkylthio group, an alkylsulfonyl group, an alkylcarbonyl group, or an alkylcarbamoyl group; and $R_4$ represents hydrogen, a chlorine atom, a cyano group, an alkaneamido group, an alkanesulfonamido group, an alkoxycarbonyl group, an alkylcarbamoyl group, an alkoxycarbonylamino group, an alkylsulfonyl group or an alkylthio group.

10. A color photographic light-sensitive element as in claim 1, wherein said silver halide emulsion layer is a green-sensitive silver halide emulsion layer.

11. A color photographic light-sensitive element as in claim 1, wherein said silver halide emulsion layer containing said magenta color-forming coupler represented by formula (I) is a green-sensitive silver halide emulsion layer, and said color photographic light-sensitive element further includes a red-sensitive silver halide emulsion layer and a blue-sensitive silver halide emulsion layer.

12. A color photographic light-sensitive element as in claim 1, wherein said silver halide emulsion layer containing said magenta color-forming coupler represented by formula (I) is a green-sensitive silver halide emulsion layer, and said color photographic light-sensitive element additionally includes a red-sensitive silver halide emulsion layer containing a phenolic or naphtholic cyan color-forming coupler, and a blue-sensitive silver halide emulsion layer containing a benzoylacetanilide or pivaloylacetanilide yellow color-forming coupler.

* * * * *